(12) United States Patent
Magno et al.

(10) Patent No.: US 10,363,066 B2
(45) Date of Patent: Jul. 30, 2019

(54) TISSUE RESECTION DEVICE

(71) Applicant: Gyrus ACMI, Inc., Southborough, MA (US)

(72) Inventors: Joey Magno, Cordova, TN (US); Saeed A. Merza, Cordova, TN (US)

(73) Assignee: Gyrus ACMI, Inc., Southborough, MA (US)

( * ) Notice: Subject to any disclaimer, the term of this patent is extended or adjusted under 35 U.S.C. 154(b) by 125 days.

(21) Appl. No.: 15/656,057

(22) Filed: Jul. 21, 2017

(65) Prior Publication Data

US 2019/0021765 A1    Jan. 24, 2019

(51) Int. Cl.
*A61B 17/42* (2006.01)
*A61B 17/3205* (2006.01)

(52) U.S. Cl.
CPC .......... *A61B 17/42* (2013.01); *A61B 17/3205* (2013.01); *A61B 2017/4216* (2013.01)

(58) Field of Classification Search
CPC ....... A61B 2017/320032; A61B 2017/320024; A61B 2017/320028; A61B 17/320783; A61B 17/32002; A61B 17/3205; A61B 17/320016; A61B 17/32053; A61B 17/320758; A61F 9/00763
See application file for complete search history.

(56) References Cited

U.S. PATENT DOCUMENTS

| | | | |
|---|---|---|---|
| 6,039,748 A | 3/2000 | Savage et al. | |
| 7,993,360 B2 | 8/2011 | Hacker et al. | |
| 8,435,259 B2* | 5/2013 | Dierck | A61B 17/32002 606/170 |
| 8,951,274 B2 | 2/2015 | Adams et al. | |
| 9,155,454 B2 | 10/2015 | Sahney et al. | |
| 9,339,288 B2 | 5/2016 | Sullivan et al. | |
| 2009/0228012 A1* | 9/2009 | Gangji | A61B 17/3472 606/80 |

(Continued)

OTHER PUBLICATIONS

"A clear advantage in uterine tissue removal". Truclear. (2015). Retrieved Jul. 20, 2017, from http://sntruclear.com/data/documents/TRUCLEAR_Brochure_US%20Only_01588.pdf, 8 pages.

(Continued)

*Primary Examiner* — Diane D Yabut
*Assistant Examiner* — Majid Jamialahmadi
(74) *Attorney, Agent, or Firm* — Harrington & Smith

(57) ABSTRACT

Disclosed herein is a medical device. The medical device includes outer, middle, and inner tubular members. The outer tubular member has a proximal end and a distal end. The middle tubular member has a proximal end and a distal end. The middle tubular member is configured to be received within the outer tubular member and capable of being rotatable relative to the outer tubular member. The inner tubular member is configured to be received within the middle tubular member and capable of reciprocating and also capable of being rotatable relative to the middle tubular member. The inner tubular member is configured to reciprocate and rotate while the middle tubular member and the outer tubular member are configured to be stationary. The middle tubular member is configured to be rotatable relative to the outer tubular member while the inner tubular member is configured to be stationary.

16 Claims, 12 Drawing Sheets

(56) References Cited

U.S. PATENT DOCUMENTS

2015/0066033 A1* 3/2015 Jorgensen .......... A61B 17/1615
606/79

OTHER PUBLICATIONS

"All-in-one Solution. For you and your patients". Hologic (2016). Retrieved Jul. 20, 2017, from http://www.myosure.com/sites/myosure/files/PB-00280-001%20Rev%20002%20MS%20Phy%20Brochure%20-%20FINAL.pdf, 7 pages.

"Reach for the Far Corners of the Uterus". Hologic (2016). Retrieved Jul. 20, 2017, from http://www.myosure.com/sites/myosure/files/MyoSure_Reach_Brochure.pdf, 3 pages.

* cited by examiner

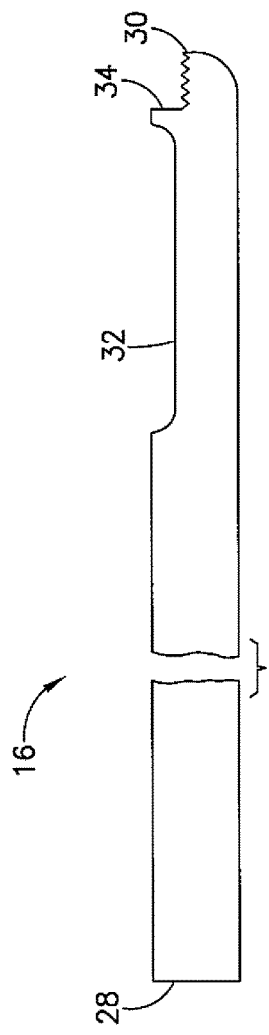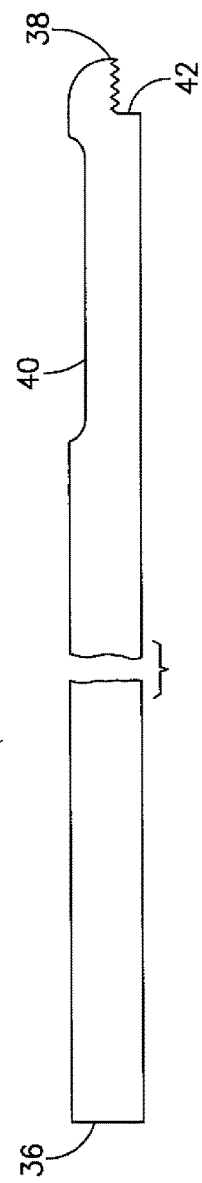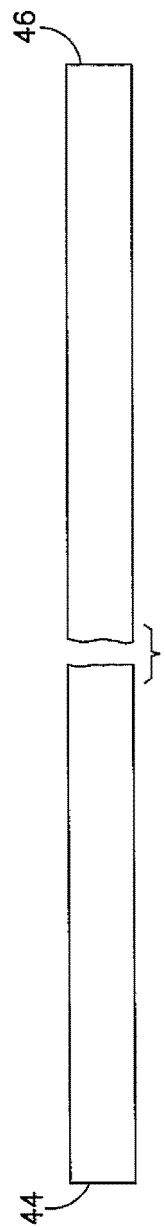

TISSUE RESECTION DEVICE

BACKGROUND

Field of the Invention

The invention relates to a tissue resection device, and more specifically relates to a tissue resection blade assembly.

Brief Description of Prior Developments

Conventional products (such as from Truclear [S&N Medtronic] and Myosure [Hologic]) participate in the treatment of resecting sub-mucosal non-cancerous growths of polyps and fibroids tissues in the uterine cavity. The areas where these unwanted tissues grow can be anywhere on the endometrium surfaces of the uterus and on the inside wall of the fundus on the upper third of the uterus.

Many of the conventional configurations require multiple blades. For example, these conventional configurations generally comprise one or more dedicated blades which are designated as an incisor blade which is generally used for resecting hard to reach areas, and another dedicated blade for resecting larger and harder tissues.

Accordingly, as the conventional designs generally result in various limitations and disadvantages (as described above), there is a need to provide improved and reliable product configurations.

SUMMARY

In accordance with one aspect of the invention, a medical device is disclosed. The medical device includes an outer tubular member, a middle tubular member, and an inner tubular member. The outer tubular member has a proximal end and a distal end. The middle tubular member has a proximal end and a distal end. The middle tubular member is configured to be received within the outer tubular member and capable of being rotatable relative to the outer tubular member. The inner tubular member is configured to be received within the middle tubular member and capable of reciprocating and also capable of being rotatable relative to the middle tubular member. The inner tubular member is configured to reciprocate and rotate while the middle tubular member and the outer tubular member are configured to be stationary. The middle tubular member is configured to be rotatable relative to the outer tubular member while the inner tubular member is configured to be stationary.

In accordance with another aspect of the invention, a cutting device for cutting tissue is disclosed. The device includes an outer tubular member, a middle tubular member, and an inner tubular member. The outer tubular member has a proximal end, a distal end, and an opening disposed at the distal end. The middle tubular member has a proximal end, a distal end, and an opening disposed at the distal end. The middle tubular member is configured to be received within the outer tubular member and capable of being rotatable relative to the outer tubular member. The inner tubular member is configured to be received within the middle tubular member and capable of reciprocating and also capable of being rotatable relative to the middle tubular member. The opening of the outer tubular member and the opening of the middle tubular member are configured to form a cutting tool when the middle tubular member rotates relative to the outer tubular member while the inner tubular member is configured to be stationary at the same time.

In accordance with another aspect of the invention, a cutting device for cutting tissue is disclosed. The device includes an outer tubular member, a middle tubular member, and an inner tubular member. The outer tubular member has a proximal end, a distal end, and an opening disposed at the distal end. The middle tubular member has a proximal end, a distal end, and an opening disposed at the distal end. The middle tubular member is configured to be received within the outer tubular member and capable of being rotatable relative to the outer tubular member. The inner tubular member is configured to be received within the middle tubular member and capable of reciprocating and also capable of being rotatable relative to the middle tubular member. The middle tubular member and the outer tubular member are configured to be stationary when the inner tubular member reciprocates and rotates relative to the middle tubular member while the opening of the outer tubular member and the opening of the middle tubular member are configured to form a closed configuration at the same time such that no liquid can flow through the two openings.

In accordance with another aspect of the invention, a cutting device for cutting tissue is disclosed. The device includes an outer tubular member, a middle tubular member, an inner tubular member, a first opening, and a second opening. The outer tubular member has a proximal end and a distal end. The middle tubular member has a proximal end and a distal end. The middle tubular member is configured to be received within the outer tubular member and capable of being rotatable relative to the outer tubular member. The inner tubular member is configured to be received within the middle tubular member and capable of reciprocating and also capable of being rotatable relative to the middle tubular member. The first opening having a cutting surface disposed at the distal end of the outer tubular member. The second opening having a cutting surface disposed at the distal end of the middle tubular member. The first opening and the second opening are configured to form one cutting tool while the inner tubular member is configured to be stationary. The inner tubular member is configured to reciprocate and rotate while the middle tubular member and the outer tubular member are configured to be stationary.

In accordance with another aspect of the invention, a cutting device for cutting tissue is disclosed. The device includes an outer tubular member, a middle tubular member, an inner tubular member, a first opening, a first window, a second opening, and a second window. The outer tubular member has a proximal end and a distal end. The middle tubular member has a proximal end and a distal end, the middle tubular member configured to be received within the outer tubular member and capable of being rotatable relative to the outer tubular member. The inner tubular member is configured to be received within the middle tubular member and capable of reciprocating and also capable of being rotatable relative to the middle tubular member. The first opening has a cutting surface disposed at the distal end of the outer tubular member. The first window is disposed between the distal end and the proximal end of the outer tubular member. The second opening has a cutting surface disposed at the distal end of the middle tubular member. The second window is disposed between the distal end and the proximal end of the middle outer tubular member. The first opening and the second opening are configured to form a cutting tool when the middle tubular member rotates relative to the outer tubular member. The inner tubular member is configured to form another cutting tool while it reciprocates and rotates relative to the middle tubular member when it is exposed by a superimposition of the first window and the second window.

BRIEF DESCRIPTION OF THE DRAWINGS

The foregoing aspects and other features of the invention are explained in the following description, taken in connection with the accompanying drawings, wherein:

FIG. 5 is a partial side view of an outer blade of the blade assembly shown in FIG. 2;

FIG. 6 is a partial side view of a middle blade of the blade assembly shown in FIG. 2;

FIG. 7 is a partial side view of an inner blade of the blade assembly shown in FIG. 2;

DETAILED DESCRIPTION

Figure 1:
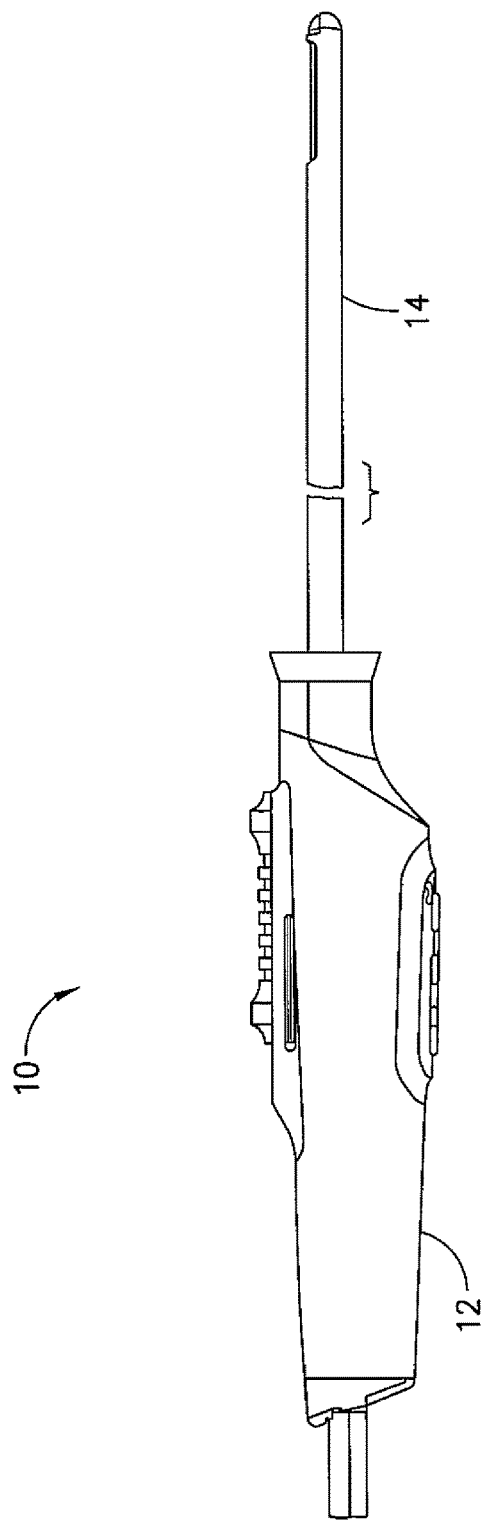
FIG. 1 is a side view of a medical device incorporating features of the invention.

Referring to FIG. 1, there is shown a side view of a medical device 10 incorporating features of the invention. Although the invention will be described with reference to the exemplary embodiments shown in the drawings, it should be understood that the invention can be embodied in many alternate forms of embodiments. In addition, any suitable size, shape or type of elements or materials could be used.

In the embodiment shown in FIG. 1, the medical device (or cutting device) 10 includes a handpiece 12 and a disposable blade assembly 14 which is removably attachable to the handpiece 12. In alternate embodiments, the medical device may comprise a stand-alone disposable blade assembly. Additionally, any other suitable configuration having a blade assembly may be provided.

Figure 2:
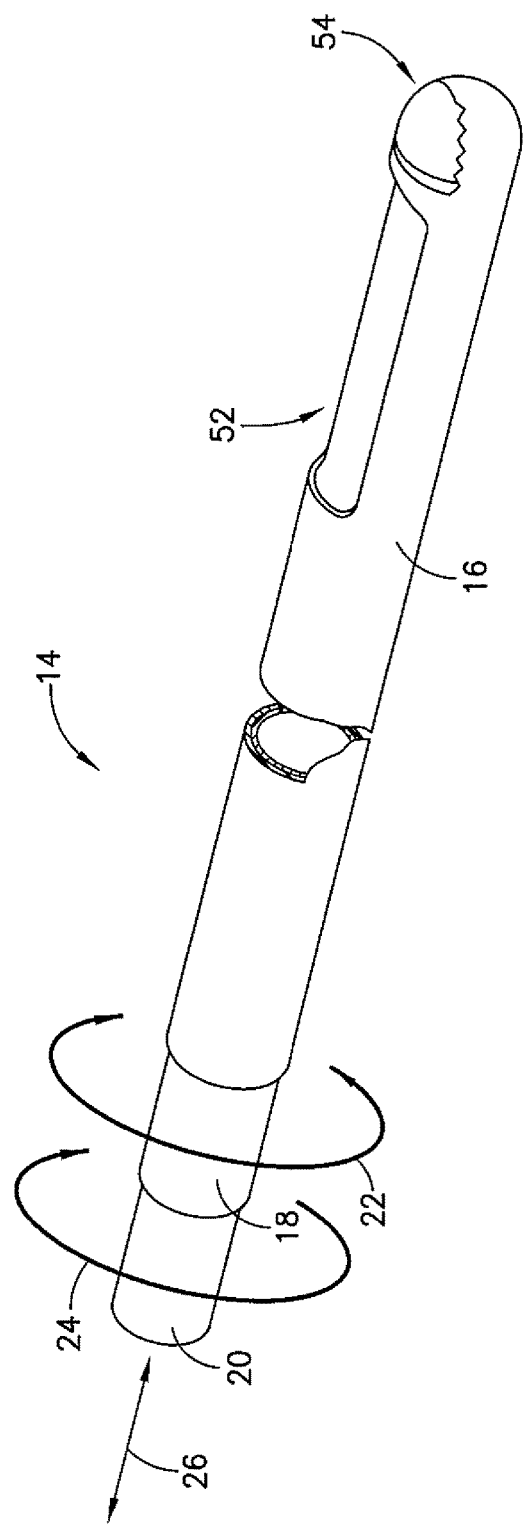
FIG. 2 is a partial perspective view of a blade assembly of the medical device shown in FIG. 1.
Figure 3:
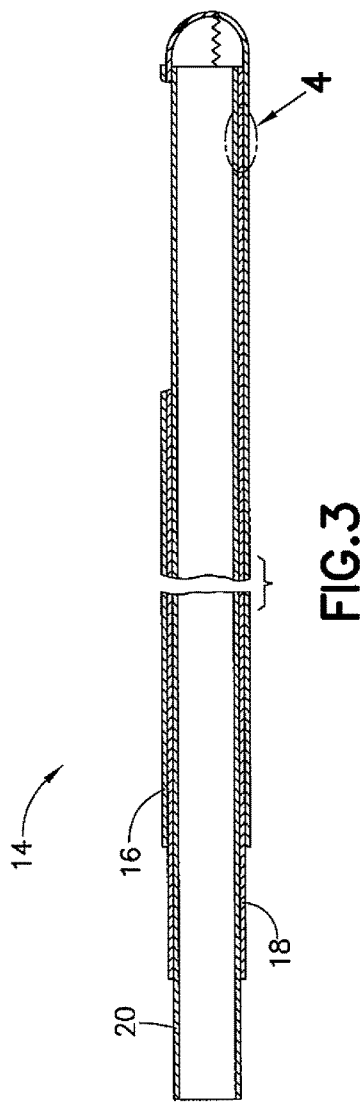
FIG. 3 is a partial section view of the blade assembly shown in FIG. 2.
Figure 4:
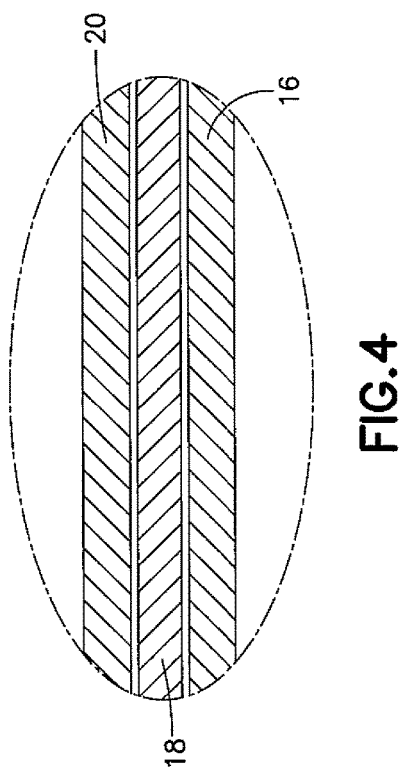
FIG. 4 is an enlarged partial section view of the portion identified as "4" in FIG. 3.

Referring now also to FIG. 2, there is shown a partial perspective view of the blade assembly 14. The blade assembly 14 comprises an outer blade 16, a middle blade 18, and an inner blade 20. The blades 14, 16, 18 each have a general tubular shape with different diameters configured such that the middle blade 18 is received by the outer blade 16, and such that the inner blade 20 is received by the middle blade 18 (see cross section view of FIG. 3 and the enlarged partial cross section view of FIG. 4 [with the identified enlarged portion labeled as "4" in FIG. 3]). Additionally, the middle blade 18 is configured to be rotatable within the outer blade 16 (see arrow 22), and the inner blade 20 is configured to be rotatable (see arrow 24) within the middle blade 18 and also capable of reciprocation (see arrow 26) within the middle blade 18. This configuration of the blade assembly 14 provides a rotary reciprocating blade window 52 and an oscillating blade window 54 proximate the end of the blade assembly 14.

Referring now to FIG. 5, the outer blade 16 is stationary and fixed all the time during operation and comprises a general tubular shape having a proximal end 28 and a distal end 30. The outer blade further comprises a first window (or opening) 32 and a second window (or opening) 34. The first window 32 is configured to be aligned with the rotary/reciprocating inner blade 20. The second window 34 is configured to be aligned with oscillating middle blade 18. The second window 34 is at the distal end 30, and the first window 32 is proximate the distal end 30 but spaced from the second window 34. According to various exemplary embodiments, edges of the window 32, 34 may comprise serrations and/or knife edges, however any suitable edge surface may be provided.

Referring now to FIG. 6, the middle blade 18 comprises a general tubular shape having a proximal end 36 and a distal end 38. The middle blade further comprises a first window (or opening) 40 and a second window (or opening) 42. The first window 40 is configured to be aligned with the first window 32 of the outer blade 16 and further provides a relief window for the rotary/reciprocating inner blade 20. The second window 42 provides an oscillating blade that has a "cutting blade" window at the end when aligned with the second window 34 of the outer blade 16. Similar to the outer blade 16, the second window 42 is at the distal end 38, and the first window 40 is proximate the distal end 38 but spaced from the second window 42. According to various exemplary embodiments, edges of the window 40, 40 may comprise serrations and/or knife edges, however any suitable edge surface may be provided. The middle blade is generally configured for cutting hard to reach tissues inside the uterus cavity. According to various embodiments, the cutting profile of the window 42 is similar to ENT and Arthroscopy shaver blades.

Referring now also to FIG. 7, the inner blade 20 forms a rotary/reciprocating blade and comprises a general tubular shape having a proximal end 44 and a distal end 46.

Figure 8:
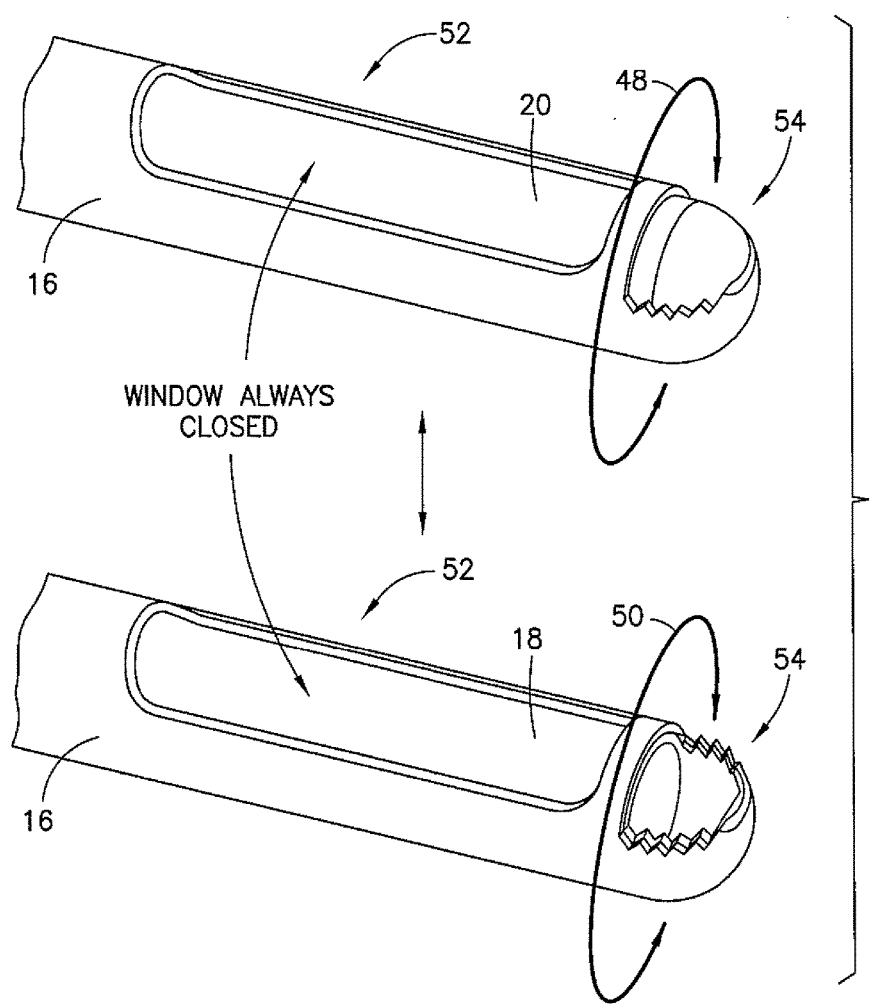
FIG. 8 shows partial perspective views of the blade assembly shown in FIG. 2 in an oscillation mode.

Referring now also to FIG. 8, during operation of an oscillation mode or single rotation mode, the inner blade 20 is in the full closed position for the middle blade 18 to start oscillating or rotating in one direction (see arrows 48, 50). This provides for the rotary reciprocating blade window 52 to remain closed while the middle blade 18 oscillates back and forth so that the oscillating blade window 54 opens and closes. This cutting operation is similar to ENT and Arthroscopy shaver blades. It should be noted that according to various exemplary embodiments, the middle blade 18 is always closed when not in-use and stops at the closed position when turned-off in order for the fluid pressure to be maintained and not depleted unnecessarily. The middle blade may enable the oscillation or one direction rotation mode of the one blade assembly.

Figure 9:
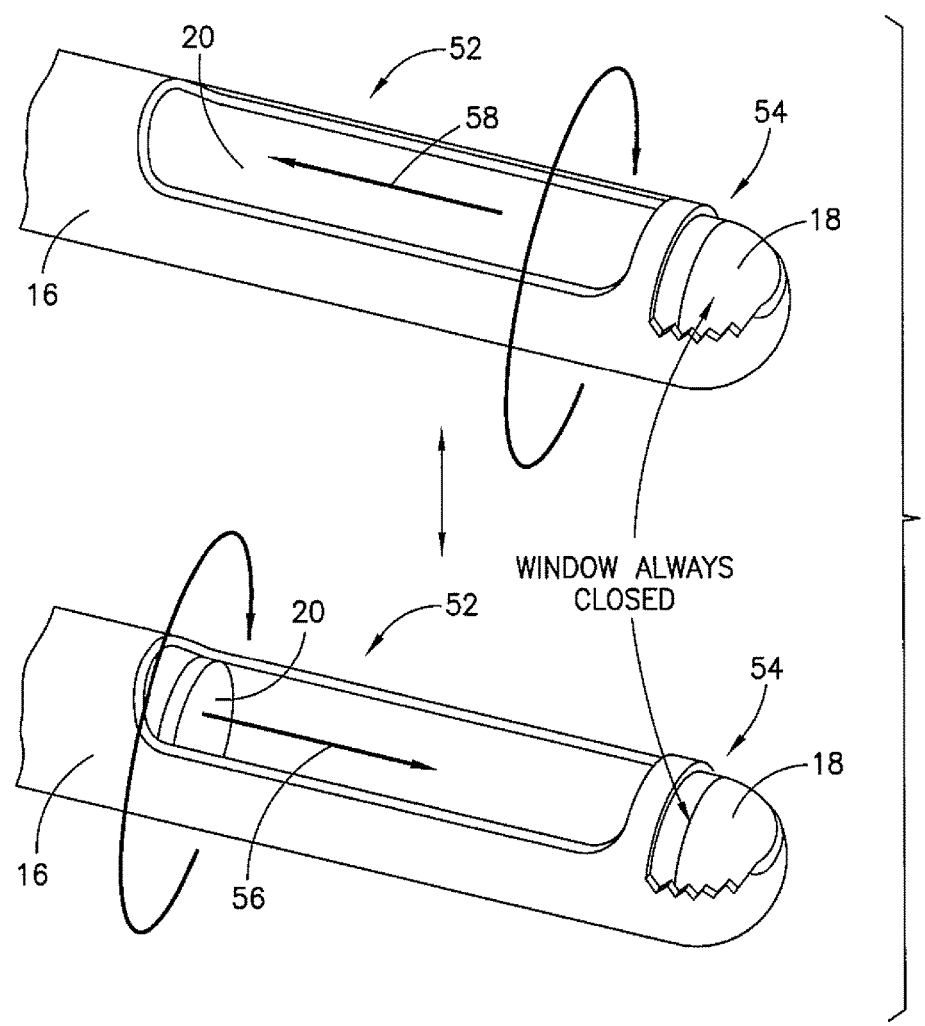
FIG. 9 shows partial perspective views of the blade assembly shown in FIG. 2 in a reciprocation and rotation mode.

Referring now also to FIG. 9, during operation of a reciprocation and rotation mode, the inner blade 20 is the rotary/reciprocating cutting blade. It is also the blade that rotates and reciprocates at the same time and performs the cutting during the forward stroke 56. In this mode, the oscillating blade window 54 remains in the close position (due to the opposite alignment of the windows 34, 42). Similar to traditional Tissue Removal Devices in the market, at this forward stroke, the inner blade rotates and that causes the slicing/cutting action to the tissue while continually providing suction function in the forward 56 and return 58 stroke. The inner blade 20 always stops at the closed (forward position) when off or not in use to prevent depletion of fluid pressure.

Figure 10:
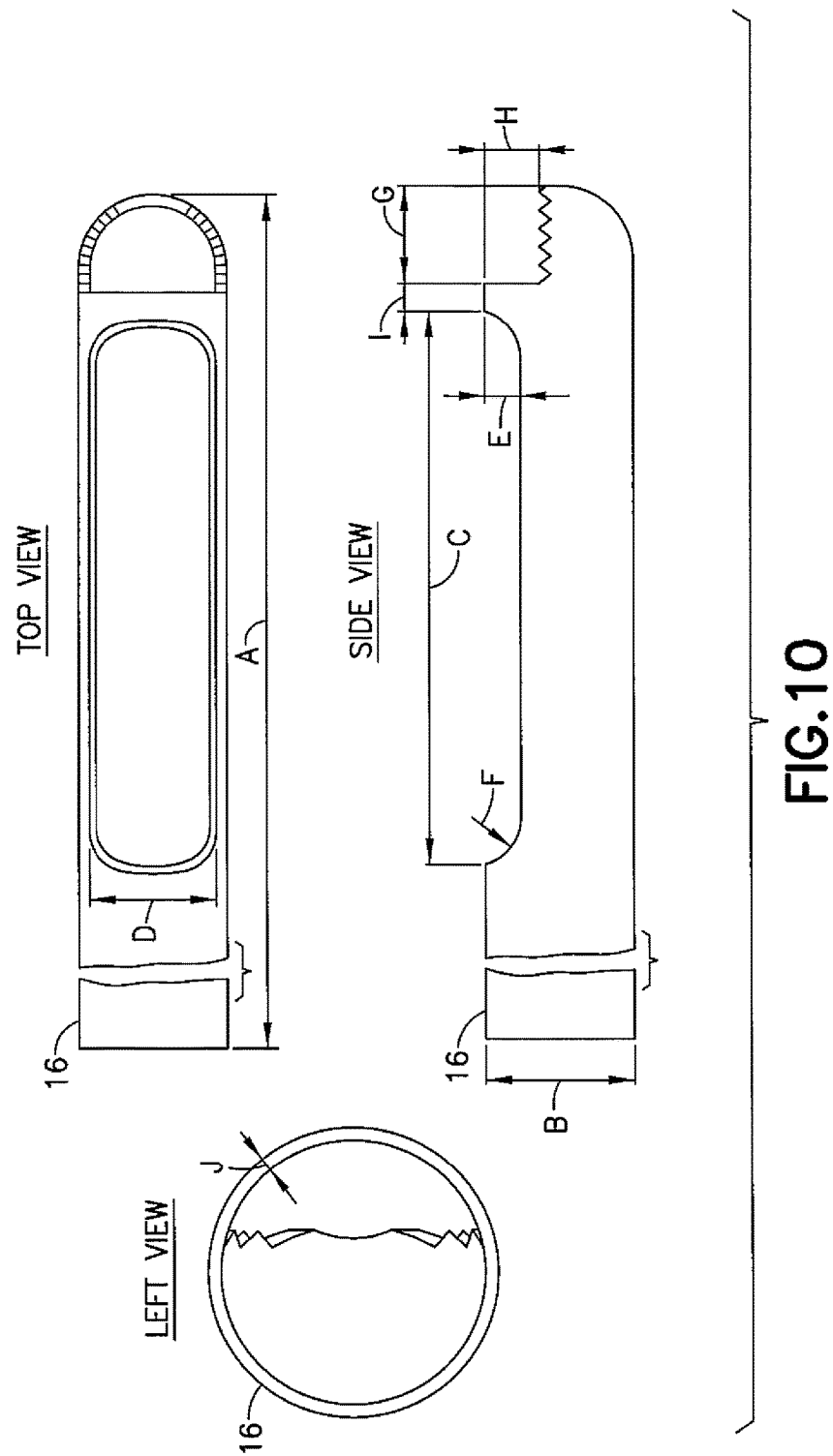
FIG. 10 shows top, left, and side views of the outer blade shown in FIG. 5.
Figure 11:
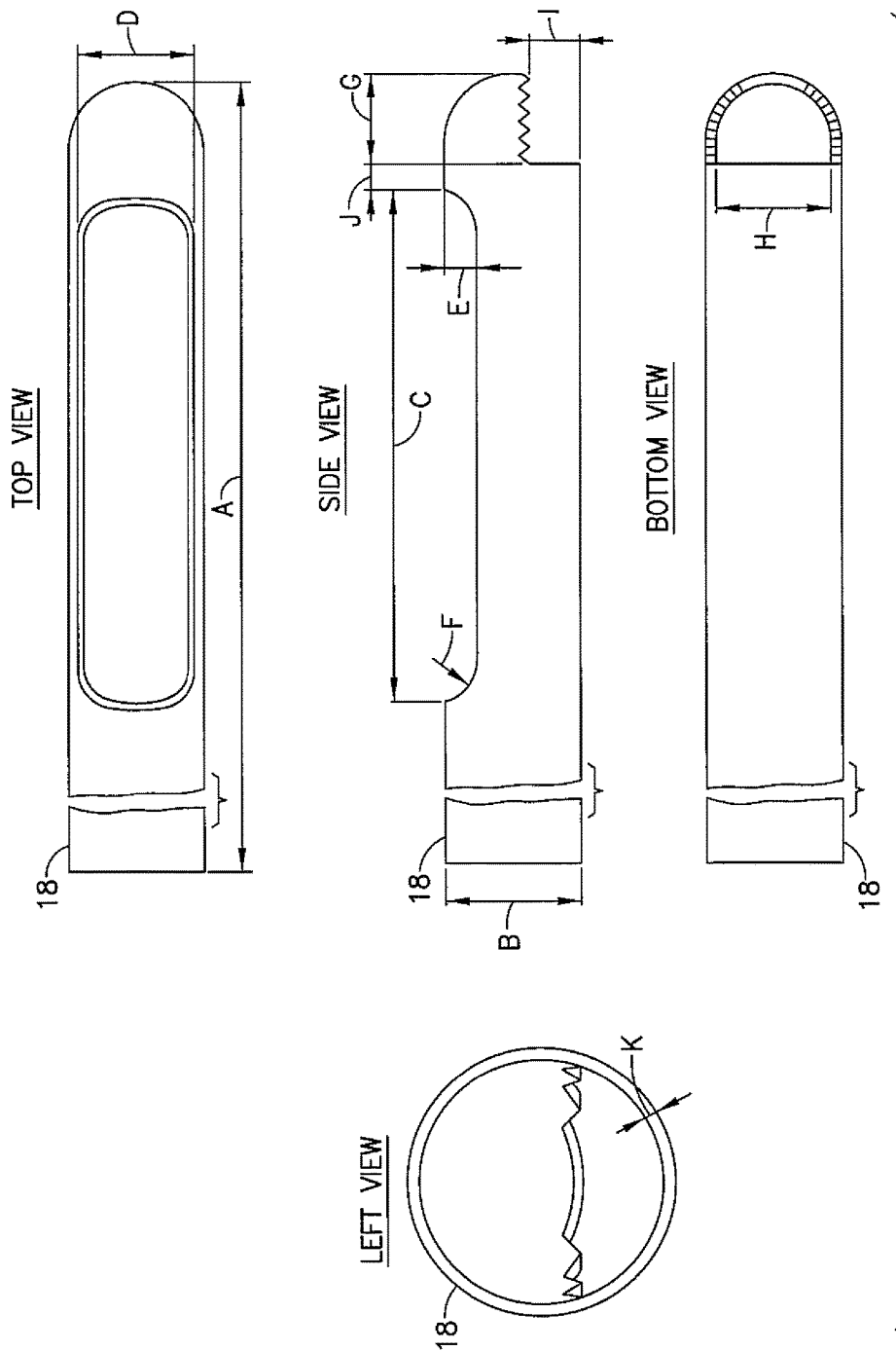
FIG. 11 shows top, left, bottom, and side views of the middle blade shown in FIG. 6.
Figure 12:
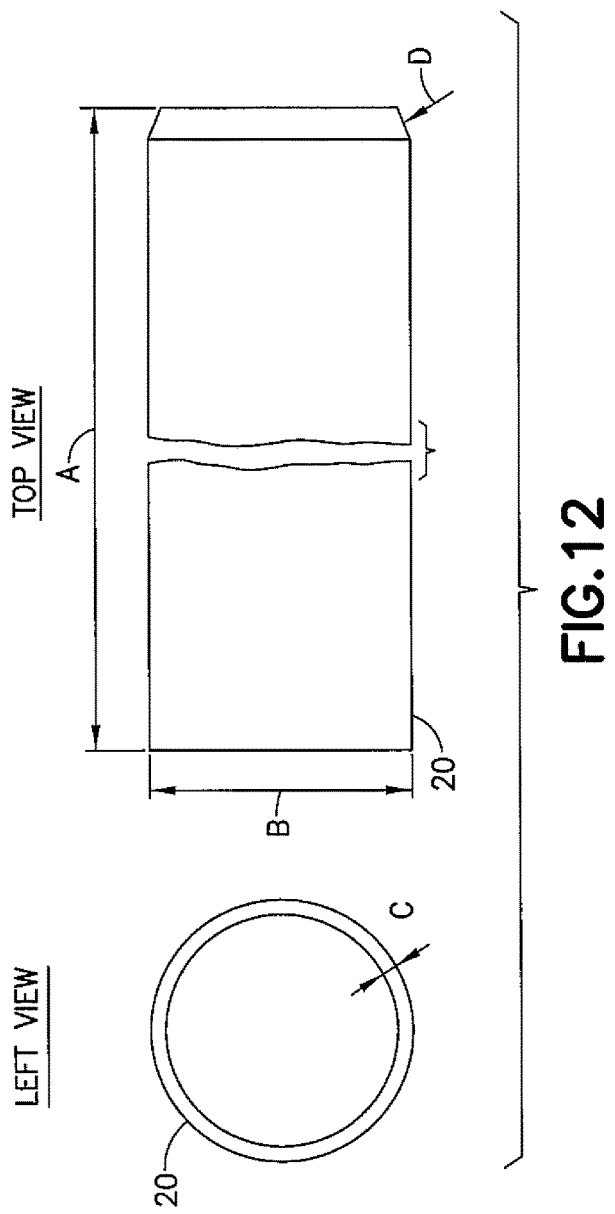
FIG. 12 shows top and left views of the inner blade shown in FIG. 7.

Referring now also to FIGS. 10-12, additional views of the outer blade 16, the middle blade 18, and the inner blade 20 are shown.

FIG. 10 illustrates a top view, a side view, and a left view of the outer blade 16. According to one or more exemplary embodiments, the outer blade 16 may comprise dimensions as follows: A (14.000 in., 355.60 mm), B (0.172 in., 4.37 mm), C (0.605 in., 15.37 mm), D (0.152 in., 3.86 mm), E (0.046 in., 1.17 mm), F (0.050 in., 1.27 mm), G (0.200 in., 5.08 mm), H (0.061 in., 1.55 mm), I (0.027 in., 0.69 mm), J (0.008 in., 0.20 mm). It should be noted that these dimensions are merely exemplary and should be considered as non-limiting examples.

FIG. 11 illustrates a top view, a side view, a bottom view, and a left view of the middle blade 18. According to one or more exemplary embodiments, the middle blade may comprise dimensions as follows: A (15.000 in., 381.00 mm), B (0.156 in., 3.96 mm), C (0.598 in., 15.19 mm), D (0.134 in., 3.40 mm), E (0.038 in., 0.97 mm), F (0.050 in., 1.27 mm), G (0.200 in., 5.08 mm), H (0.138 in., 3.51 mm), I (0.053 in., 1.35 mm), J (0.030 in., 0.76 mm), K (0.008 in., 0.20 mm). It should be noted that these dimensions are merely exemplary and should be considered as non-limiting examples.

FIG. 12 illustrates a top view and a left view of the inner blade 20. According to one or more exemplary embodiments, the inner blade may comprise dimensions as follows: A (17.000 in., 431.80 mm), B (0.141 in., 3.58 mm), C (0.006 in., 0.15 mm), D (Chamfer dimensions as desired to create sharp end). It should be noted that these dimensions are merely exemplary and should be considered as non-limiting examples.

Figure 13:
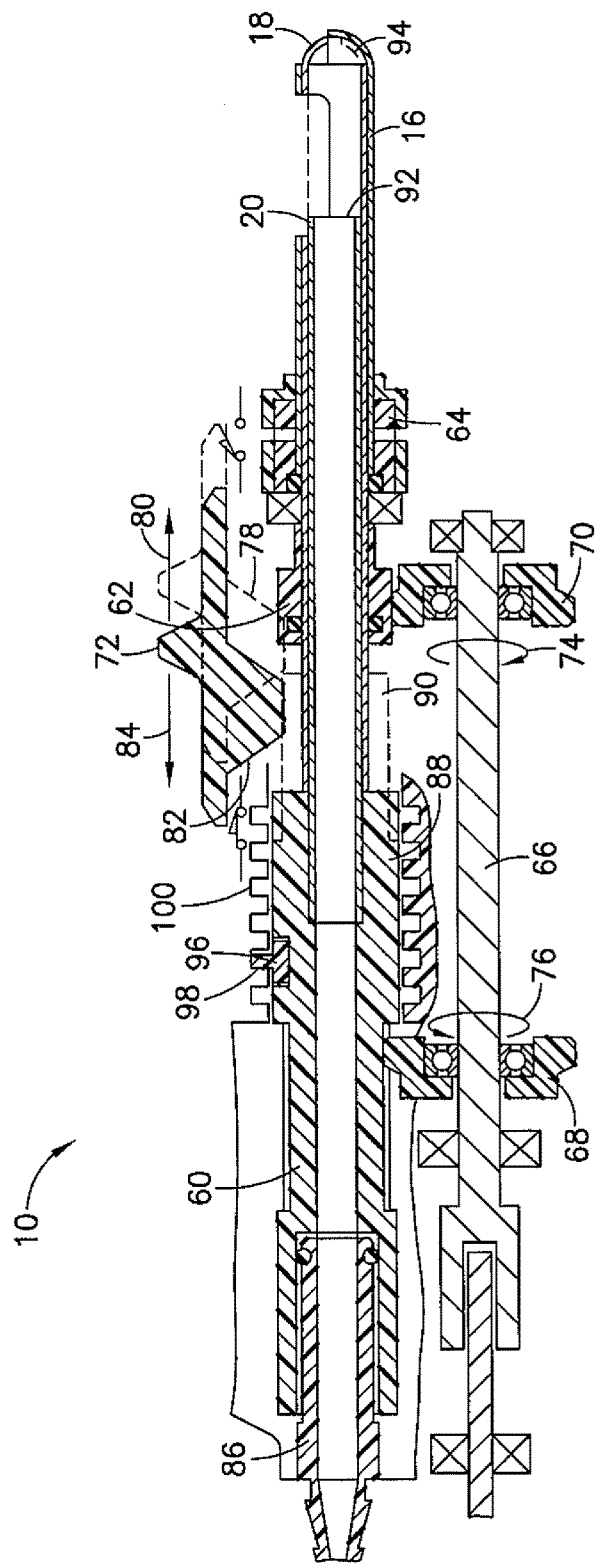
FIG. 13 is a partial cross-section view of the medical device shown in FIG. 1.

Referring now also to FIG. 13, there is shown a cross-section view of the cutting device 10. According to one or more exemplary embodiments, the cutting device 10 comprises an inner blade driver 60, a middle blade driver 62, an outer blade fixing member 64, a rotatable shaft 66, a first one way bearing 68, a second one way bearing 70, and a movable member 72.

The inner blade driver 60 is connected to an end of the inner blade 20 and is configured to rotate and reciprocate the inner blade 20. The middle blade driver 62 is connected to the middle blade 18 and is configured to rotate the middle blade 18 in one direction. The outer blade fixing member 64 is connected to the outer blade 16 and is configured to maintain the outer blade 16 in a stationary position.

The rotatable shaft 66 is substantially parallel to and adjacent the blades 16, 18, 20 and is configured to be rotatable in a clockwise (CW) direction 74 and a counter-clockwise (CCW) direction 76. The first one way bearing 68 is mounted on one end of the shaft 66 and contacts the inner blade driver 60. The second one way bearing 70 is mounted on an opposite end of the shaft 66 and contacts the middle blade driver 62.

At least a portion of the movable member 72 is between the inner blade driver 60 and the middle blade driver 62 and is configured to be movable between a forward position 78 (when moved in direction 80) and a rear position 82 (when moved in direction 84).

When the movable member 72 is in the forward position 78, this locks the middle blade 18 in the closed position and also causes the device 10 to rotate the shaft 66 in the CCW direction 76. With the shaft 66 rotating in the CCW direction 76, this causes the first one way bearing 68 to engage with and rotate the inner blade driver 60, while at the same time causing the second one way bearing 70 to disengage with the middle blade driver 60 (and provide no turning force to the middle blade driver 60).

When the movable member 72 is in the rear position 82, this locks the inner blade 20 in the closed position and also causes the device 10 to rotate the shaft 66 in the CW direction 74. With the shaft 66 rotating in the CW direction 74, this causes the second one way bearing 70 to engage with and rotate the middle blade driver 62, while at the same time causing the first one way bearing 68 to disengage with the inner blade driver 60 (and provide no turning force to the inner blade driver 60).

Figure 14:
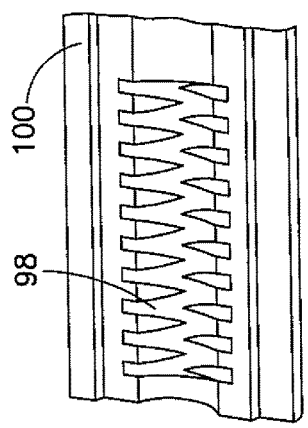
FIG. 14 is a perspective view of a portion of a housing of the medical device shown in FIG. 1, 13.
Figure 15:
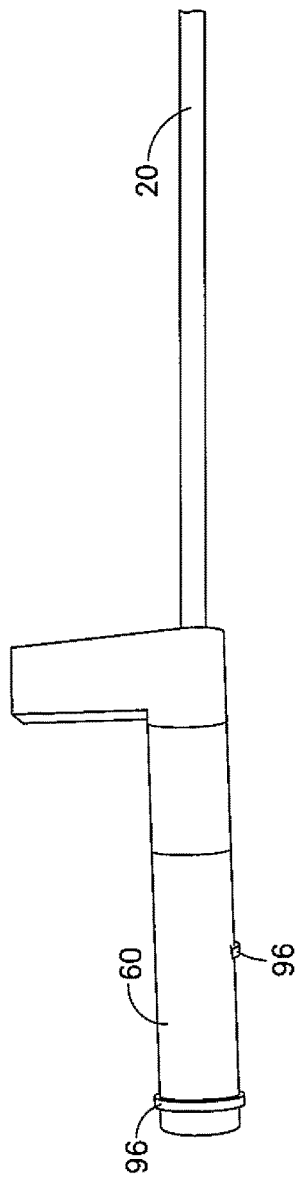
FIG. 15 is a perspective view of an inner blade driver and the inner blade of the medical device shown in FIG. 1, 13.
Figure 17:
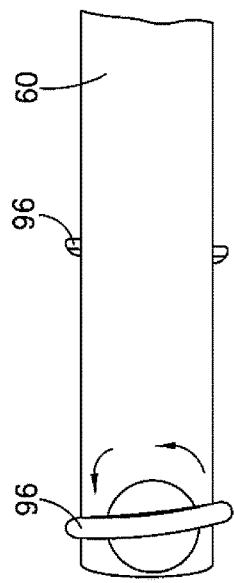
FIGS. 16-18 show partial perspective views of the inner blade driver shown in FIG. 15.
Figure 18:
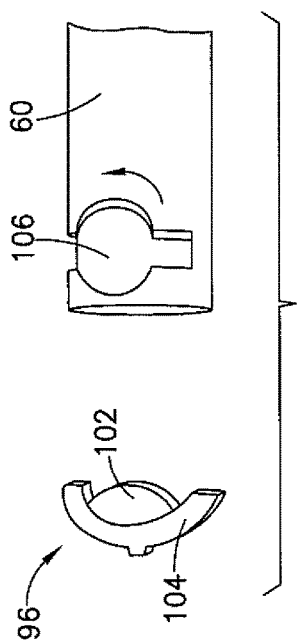
Figure 16:
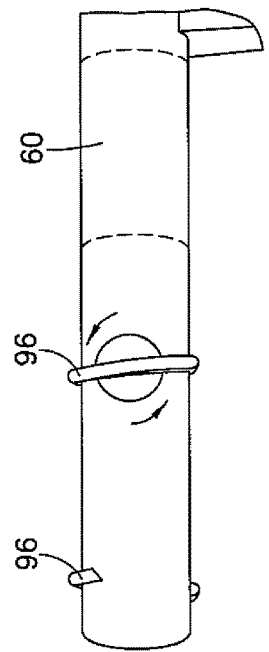

Furthermore, the inner blade driver (or translation piece) 60 is configured to reciprocate through the housing 100 with projecting members 96 alternating back and forth through a double helical sweep configuration 98 on the housing 100 (see also FIGS. 14, 15). Additionally, element 86 is configured to be a fixed component of a suction barb fitting, while the O-ring provides a seal when the inner blade driver 60 reciprocates back and forth. Referring now also to FIGS. 16-18, each projecting member 96 is configured to be movably connected to the inner blade driver 60. Each projecting member 96 comprises a connecting portion 102 and a projecting portion 104. The connecting portion 102 is configured to be received at a receiving area 106 of the inner blade driver 60. The projecting portion 104 comprises a general arc or curved shape and is configured to be received at the double helical sweep 98 of the housing 100. As shown in FIGS. 16 and 17, due to the curved shape of the projecting portion extending along approximately half of the circumference of the inner blade driver 60, one of the projecting members 96 is configured to be received at the double helical sweep 98 of one side of the housing 100 and the other one of the projecting members 96 is configured to be received at the double helical sweep 98 of the other side of the housing 100. The projecting members 96 are configured to pivot (at the movable connection between the connecting portion 102 and the receiving area 106) at an angle that follows the double helical sweep pitch angle in order to reciprocate and rotate the inner blade driver 60 back and forth. When the projecting members 96 move forward through the double helical sweep 98, the inner blade driver is configured to move from a first position 88 to a second position 90, which in turn moves the inner blade 20 from an open position 92 to a closed position 94. When the projecting members 96 move back through the double helical sweep 98, the inner blade driver is configured to move from the second position 90 to the first position 88, which in turn moves the inner blade 20 from the closed position 94 to the open position 92.

While the one or more exemplary embodiments have been described above in connection with the configuration shown in FIG. 13, one skilled in the art will appreciate that the various exemplary embodiments are not necessarily so limited and that alternate configurations for driving the blades could be provided. For example, in some embodiments the middle blade driver 62 may be configured to provide for one direction rotation only of the middle blade (with no oscillation), while in other embodiments the middle blade driver may provide for oscillation only or oscillation and rotation of the middle blade.

Technical effects of any one or more of the exemplary embodiments provide significant advantages over conventional configurations (such as blades for Hysterescopic Morcellation or Tissue Removal devices) having multiple blade assemblies. The exemplary embodiment disclosed herein provides a very simple construction where one blade assembly is able to accommodate all different versions (of the different blade assemblies) that the competitors offer. This one blade assembly can function in two different independent modes such as oscillation mode and reciprocation/rotation mode to provide a Tissue Resection Blade for hard to reach polyps and fibroids.

Additional technical effects of any one or more of the exemplary embodiments eliminate the need for multiple blade types as descried above. This will enable the GYN surgeon, for example, to not have to switch back and forth to different blades during the operation thereby saving procedure time. The hospital or healthcare provider facility will also save on their inventory by stocking one single blade assembly SKU instead of multiple blades or blade assemblies. The various exemplary embodiments may also be applicable in other shaver operation(s) such as in ENT or Arthroscopy.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced or utilized in any combination (e.g., any combination that is suitable, practicable and/or feasible) and are not limited only to those combinations described herein and/or included in the appended claims.

In one exemplary embodiment, a medical device, the device comprising: an outer tubular member having a proximal end and a distal end; a middle tubular member having a proximal end and a distal end, the middle tubular member configured to be received within the outer tubular member and capable of being rotatable relative to the outer tubular member; and an inner tubular member configured to be received within the middle tubular member and capable of reciprocating and also capable of being rotatable relative to the middle tubular member; wherein the inner tubular member is configured to reciprocate and rotate while the middle tubular member and the outer tubular member are configured to be stationary, and wherein the middle tubular member is configured to be rotatable relative to the outer tubular member while the inner tubular member is configured to be stationary.

A device as above wherein the outer tubular member comprises a first opening, wherein the middle tubular member comprises a second opening, and wherein the first opening is aligned with the second opening.

A device as above wherein the outer tubular member comprises a first window between the first opening and the proximal end, wherein the middle tubular member comprises a second window between the second opening and the proximal end.

A device as above wherein the first window and the second window are aligned with each other.

In another exemplary embodiment, a cutting device for cutting tissue, the device comprising: an outer tubular member having a proximal end, a distal end, and an opening disposed at the distal end; a middle tubular member having a proximal end, a distal end, and an opening disposed at the distal end, the middle tubular member configured to be received within the outer tubular member and capable of being rotatable relative to the outer tubular member; and an inner tubular member configured to be received within the middle tubular member and capable of reciprocating and also capable of being rotatable relative to the middle tubular member; wherein the opening of the outer tubular member and the opening of the middle tubular member are configured to form a cutting tool when the middle tubular member rotates relative to the outer tubular member while the inner tubular member is configured to be stationary at the same time.

A device as above wherein the outer tubular member is configured to remain stationary during operation.

A device as above wherein the outer tubular member comprises a first window between the opening and the proximal end, wherein the middle tubular member comprises a second window between the opening and the proximal end.

A device as above wherein the first window and the second window are aligned with each other.

In another exemplary embodiment, a cutting device for cutting tissue, the device comprising: an outer tubular member having a proximal end, a distal end, and an opening disposed at the distal end; a middle tubular member having a proximal end, a distal end, and an opening disposed at the distal end, the middle tubular member configured to be received within the outer tubular member and capable of being rotatable relative to the outer tubular member; and an inner tubular member configured to be received within the middle tubular member and capable of reciprocating and also capable of being rotatable relative to the middle tubular member; wherein the middle tubular member and the outer tubular member are configured to be stationary when the inner tubular member reciprocates and rotates relative to the middle tubular member while the opening of the outer tubular member and the opening of the middle tubular member are configured to form a closed configuration at the same time such that no liquid can flow through the two openings.

A device as above wherein the outer tubular member comprises a first window between the first opening and the proximal end, wherein the middle tubular member comprises a second window between the second opening and the proximal end.

A device as above wherein the first window and the second window are aligned with each other.

A device as above wherein the distal end of the middle tubular member is between the proximal end and distal end of the outer tubular member.

In another exemplary embodiment, a cutting device for cutting tissue, the device comprising: an outer tubular member having a proximal end and a distal end; a middle tubular member having a proximal end and a distal end, the middle tubular member configured to be received within the outer tubular member and capable of being rotatable relative to the outer tubular member; an inner tubular member configured to be received within the middle tubular member and capable of reciprocating and also capable of being rotatable relative to the middle tubular member; a first opening with cutting surface disposed at the distal end of the outer tubular member; and a second opening with cutting surface disposed at the distal end of the middle tubular member; wherein the first opening and the second opening are configured to form one cutting tool while the inner tubular member is configured to be stationary, and wherein the inner tubular member is configured to reciprocate and rotate while the middle tubular member and the outer tubular member are configured to be stationary.

A device as above wherein the first opening and the second opening are also configured to form a closed configuration at the same time such that the two openings are liquid tight.

A device as above wherein the outer tubular member comprises a first window between the first opening and the proximal end, wherein the middle tubular member comprises a second window between the second opening and the proximal end.

A device as above wherein the first window and the second window are aligned with each other.

In another exemplary embodiment, a cutting device for cutting tissue, the device comprising: an outer tubular member having a proximal end and a distal end; a middle tubular member having a proximal end and a distal end, the middle tubular member configured to be received within the outer tubular member and capable of being rotatable relative to the outer tubular member; an inner tubular member configured to be received within the middle tubular member and capable of reciprocating and also capable of being rotatable relative to the middle tubular member; a first opening with a cutting surface disposed at the distal end of the outer tubular member; and a first window disposed between the distal end and the proximal end of the outer tubular member; a second opening with a cutting surface disposed at the distal end of the middle tubular member, a second window disposed between the distal end and the proximal end of the middle outer tubular member; wherein the first opening and the second opening are configured to form a cutting tool when the middle tubular member rotates relative to the outer tubular member, and wherein the inner tubular member is configured to form another cutting tool while it reciprocates and rotates relative to the middle tubular member when it is exposed by a superimposition of the first window and the second window.

A device as above wherein the outer tubular member is configured to remain stationary during operation.

A device as above wherein the middle tubular member is configured to oscillate, or rotate in only one direction, within the outer tubular member.

A device as above wherein the distal end of the middle tubular member is between the proximal end and distal end of the outer tubular member.

It should be understood that components of the invention can be operationally coupled or connected and that any number or combination of intervening elements can exist (including no intervening elements). The connections can be direct or indirect and additionally there can merely be a functional relationship between components.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. A medical device, the device comprising:
   an outer tubular member having a proximal end and a distal end;
   a middle tubular member having a proximal end and a distal end, the middle tubular member configured to be received within the outer tubular member and capable of being rotatable relative to the outer tubular member; and
   an inner tubular member configured to be received within the middle tubular member and capable of reciprocating and also capable of being rotatable relative to the middle tubular member;
   wherein the outer tubular member comprises a first opening, wherein the middle tubular member comprises a second opening, and wherein the first opening is aligned with the second opening, wherein the outer tubular member comprises a first window between the first opening and the proximal end, wherein the middle tubular member comprises a second window between the second opening and the proximal end,
   wherein the inner tubular member is configured to reciprocate and rotate while the middle tubular member and the outer tubular member are configured to be stationary, and wherein the middle tubular member is configured to be rotatable relative to the outer tubular member while the inner tubular member is configured to be stationary.

2. A medical device as in claim 1 wherein the first window and the second window are aligned with each other.

3. A cutting device for cutting tissue, the device comprising:
   an outer tubular member having a proximal end, a distal end, and a first opening disposed at the distal end;
   a middle tubular member having a proximal end, a distal end, and a second opening disposed at the distal end, the middle tubular member configured to be received within the outer tubular member and capable of being rotatable relative to the outer tubular member; and
   an inner tubular member configured to be received within the middle tubular member and capable of reciprocating and also capable of being rotatable relative to the middle tubular member;
   wherein the outer tubular member comprises a first window between the first opening and the proximal end, wherein the middle tubular member comprises a second window between the second opening and the proximal end,
   wherein the first opening of the outer tubular member and the second opening of the middle tubular member are configured to form a cutting tool when the middle tubular member rotates relative to the outer tubular member while
the inner tubular member is configured to be stationary at the same time.

4. A cutting device as in claim 3 wherein the outer tubular member is configured to remain stationary during operation.

5. A cutting device as in claim 3 wherein the first window and the second window are aligned with each other.

6. A cutting device for cutting tissue, the device comprising:
   an outer tubular member having a proximal end, a distal end, and a first opening disposed at the distal end;
   a middle tubular member having a proximal end, a distal end, and a second opening disposed at the distal end, the middle tubular member configured to be received within the outer tubular member and capable of being rotatable relative to the outer tubular member; and
   an inner tubular member configured to be received within the middle tubular member and capable of reciprocating and also capable of being rotatable relative to the middle tubular member;

wherein the middle tubular member and the outer tubular member are configured to be stationary when the inner tubular member reciprocates and rotates relative to the middle tubular member while the first opening of the outer tubular member and the second opening of the middle tubular member are facing in opposite directions to form a closed configuration such that no liquid can flow through the first opening of the outer tubular member.

7. A cutting device as in claim 6 wherein the outer tubular member comprises a first window between the first opening and the proximal end, wherein the middle tubular member comprises a second window between the second opening and the proximal end.

8. A cutting device as in claim 7 wherein the first window and the second window are aligned with each other.

9. A cutting device as in claim 6 wherein the distal end of the middle tubular member is between the proximal end and distal end of the outer tubular member.

10. A cutting device for cutting tissue, the device comprising:
an outer tubular member having a proximal end and a distal end;
a middle tubular member having a proximal end and a distal end, the middle tubular member configured to be received within the outer tubular member and capable of being rotatable relative to the outer tubular member;
an inner tubular member configured to be received within the middle tubular member and capable of reciprocating and also capable of being rotatable relative to the middle tubular member;
a first opening with cutting surface disposed at the distal end of the outer tubular member; and
a second opening with cutting surface disposed at the distal end of the middle tubular member;
wherein the first opening and the second opening are configured to form one cutting tool while the inner tubular member is configured to be stationary, wherein the inner tubular member is configured to reciprocate and rotate while the middle tubular member and the outer tubular member are configured to be stationary, and wherein the first opening and the second opening are configured to form a closed configuration when the openings are facing in opposite directions such that no liquid can flow through the first opening.

11. A cutting device as in claim 10 wherein the outer tubular member comprises a first window between the first opening and the proximal end, wherein the middle tubular member comprises a second window between the second opening and the proximal end.

12. A cutting device as in claim 11 wherein the first window and the second window are aligned with each other.

13. A cutting device for cutting tissue, the device comprising:
an outer tubular member having a proximal end and a distal end;
a middle tubular member having a proximal end and a distal end, the middle tubular member configured to be received within the outer tubular member and capable of being rotatable relative to the outer tubular member;
an inner tubular member configured to be received within the middle tubular member and capable of reciprocating and also capable of being rotatable relative to the middle tubular member;
a first opening with a cutting surface disposed at the distal end of the outer tubular member; and
a first window disposed between the distal end and the proximal end of the outer tubular member;
a second opening with a cutting surface disposed at the distal end of the middle tubular member,
a second window disposed between the distal end and the proximal end of the middle outer tubular member;
wherein the first opening and the second opening are configured to form a cutting tool when the middle tubular member rotates relative to the outer tubular member, and wherein the inner tubular member is configured to form another cutting tool while it reciprocates and rotates relative to the middle tubular member when it is exposed by a superimposition of the first window and the second window.

14. A cutting device as in claim 13 wherein the outer tubular member is configured to remain stationary during operation.

15. A cutting device as in claim 13 wherein the middle tubular member is configured to oscillate, or rotate in only one direction, within the outer tubular member.

16. A cutting device as in claim 13 wherein the distal end of the middle tubular member is between the proximal end and distal end of the outer tubular member.

* * * * *